(12) United States Patent
Mori et al.

(10) Patent No.: US 7,711,080 B2
(45) Date of Patent: May 4, 2010

(54) COMPUTED TOMOGRAPHY METHOD AND APPARATUS FOR A DYNAMIC IMAGE OF A MOVING SITE

(75) Inventors: Shinichirou Mori, Chiba (JP); Masahiro Endo, Chiba (JP)

(73) Assignee: National Institute of Radiological Sciences, Chiba-shi (JP)

( * ) Notice: Subject to any disclaimer, the term of this patent is extended or adjusted under 35 U.S.C. 154(b) by 166 days.

(21) Appl. No.: 11/918,521

(22) PCT Filed: Oct. 19, 2005

(86) PCT No.: PCT/JP2005/019174

§ 371 (c)(1),
(2), (4) Date: Oct. 15, 2007

(87) PCT Pub. No.: WO2006/114908

PCT Pub. Date: Nov. 2, 2006

(65) Prior Publication Data

US 2009/0067570 A1  Mar. 12, 2009

(30) Foreign Application Priority Data

Apr. 25, 2005  (JP) .............................. 2005-127123

(51) Int. Cl.
*G01N 23/083* (2006.01)
*H05G 1/62* (2006.01)

(52) U.S. Cl. ................................. 378/8; 378/15; 378/95

(58) Field of Classification Search ...................... 378/4, 378/8, 15, 19, 95, 114; 600/425, 428
See application file for complete search history.

(56) References Cited

U.S. PATENT DOCUMENTS

| 4,530,109 | A | * | 7/1985 | Klausz ........................... 378/8 |
| 6,269,140 | B1 | * | 7/2001 | Takagi et al. |
| 6,522,712 | B1 | * | 2/2003 | Yavuz et al. .................... 378/4 |
| 6,628,742 | B2 | * | 9/2003 | Pan et al. ........................ 378/8 |
| 7,054,405 | B2 | * | 5/2006 | Edic et al. ....................... 378/4 |
| 7,058,440 | B2 | * | 6/2006 | Heuscher et al. ............. 600/428 |
| 7,127,025 | B2 | * | 10/2006 | Bruder et al. ................... 378/8 |
| 7,177,386 | B2 | * | 2/2007 | Mostafavi et al. .............. 378/4 |
| 7,376,214 | B2 | * | 5/2008 | Klingenbeck-Regn ......... 378/8 |
| 2004/0077941 | A1 | * | 4/2004 | Reddy et al. ................. 600/428 |

FOREIGN PATENT DOCUMENTS

| JP | A-07-313504 | * | 12/1995 |
| JP | A-09-075338 | * | 3/1997 |
| JP | A-10-328175 | * | 12/1998 |
| JP | A-2001-198121 | * | 7/2001 |

* cited by examiner

*Primary Examiner*—IRakli Kiknadze
*Assistant Examiner*—Thomas R Artman
(74) *Attorney, Agent, or Firm*—Oliff & Berridge, PLC

(57) ABSTRACT

When a repeatedly periodically moving site of a to-be-examined subject in a gantry is subjected to computed tomography and is reconstructed, the gantry is rotated in synchronization with the movement of the periodically moving site, and a dynamic image showing a transient phenomenon is obtained in which the periodic movement of the moving site has been stopped. As a result, the flow of a contrast agent or the like can be observed in a state of stopping the movement of an internal organ that moves repeatedly periodically.

9 Claims, 6 Drawing Sheets (A)
Axial cross-section (B)
Coronal cross-section (C)
Sagital cross-section

COMPUTED TOMOGRAPHY METHOD AND APPARATUS FOR A DYNAMIC IMAGE OF A MOVING SITE

TECHNICAL FIELD

The present invention relates to a computed tomography method and a computed tomography apparatus for taking a dynamic image of a repeatedly periodically moving site of a to-be-examined subject in a gantry by subjecting the moving site to computed tomography for segment reconstruction. More particularly, the present invention relates to a computed tomography method and a computed tomography apparatus for a dynamic image of a moving site suitable to be used when the heart or the lungs are examined radiographically.

BACKGROUND ART

In general, when a moving object is photographed according to computed tomography, a motion artifact resulting from its motion appears in an image obtained by the tomography. The reason why such a motion artifact appears is that the computed tomography has a low temporal resolution with respect to the speed of the moving object. Therefore, the temporal resolution is heightened as follows. That is, (1) the rotational speed of a computed tomography apparatus (CT apparatus) is increased for a rapidly moving or vibrating organ, such as a heart, so as to have a rotation time of, for example, 0.5 seconds or less, or (2) an algorithm (half scanning) is performed to reduce the number of projection images by, for example, half, and these projection images are used when images corresponding to one rotation are reconstructed such that data acquired by one rotation is divided for each cardiac phase, and then pieces of data having the same cardiac phases are collected from data obtained through a plurality of scanning operations. These techniques make it possible to observe a time-dependent movement (i.e., a movement changing with the lapse of time).

On the other hand, a segment reconstruction algorithm is employed for a periodically moving or vibrating organ, such as a heart. According to this segment reconstruction algorithm, projection images that are different in the X-ray tube view angle of a computed tomographic image and that are the same in the expanding and contracting phase of the heart are collected and reconstructed. For this, if the heartbeat and the computed tomography rotation time (hereinafter, referred to as "CT rotation time") coincide with each other, all X-ray tube view angles become equal to each other as shown in FIGS. 1(A) and 2 (i.e., 180 degrees in the example of FIG. 1(A), and 0 degrees and 180 degrees in the example of FIG. 2), and hence data for one rotation cannot be acquired, thus making it impossible to form an image. Therefore, various measures have been carried out. For example, the CT rotation time is changed so that the heartbeat of a subject, such as a patient, obtained from an electrocardiogram does not coincide with the CT rotation time as shown in FIGS. 1(B) and 3, and, as a result, synchronized projection images are not used (see Japanese Published Unexamined Patent Application Nos. H7-313504, H10-328175, and 2001-198121.)

In FIGS. 2 and 3, reference numeral 10 designates a patient, reference numeral 20 designates a gantry of a computed tomography apparatus (also called a "CT gantry"), reference numeral 22 designates an X-ray tube, and reference numeral 24 designates a scintillator arranged two-dimensionally.

However, conventionally, a transient movement, such as the flow of a contrast agent in a contrast examination, the movement of a catheter in a catheterization examination or a surgical operation, the movement of an insertion tube, or the movement of food and drink, was not able to be observed.

Japanese Published Unexamined Patent Application No. H9-75338, which is recognized as relating to this conventional technique, discloses a method in which, if the heartbeat is changed during photography of the heart, the rotation time is changed in accordance with a change in the heartbeat so as to improve the accuracy of ECG-gated segment reconstruction. Cardiac computed tomography is usually carried out while holding patient's breath for ten-odd seconds, and hence the heart rate inevitably becomes higher toward the last half of the tomography.

However, this method aims to obtain a three-dimensional image. Even if an image in which a cardiac phase has been changed is formed, there will be a difference in absolute time between CT slices. Therefore, it is impossible to see how a contrast agent or the like dyes.

Additionally, a cardiac muscle perfusion examination is performed according to a MRI method or a PET method, and has an important place in the cardiac examination.

If a cardiac muscle perfusion examination is performed according to the conventional computed tomography method, helical scanning or step & shoot scanning (which is repeatedly performed such that a patient is subjected to computed axial tomography at a position where the patient is lying, and is then subjected to axial tomography at a next position) is performed when ECG-gated or non-ECG-gated computed tomography is performed. Therefore, a time lag occurs between the photographing time of the apex of the heart and the photographing time of the bottom thereof. In addition, the influence of the heartbeat on image quality cannot be completely eliminated (i.e., an artifact does not disappear) even if ECG-gated computed tomography is performed, and hence the image quality is worsened, and the reliability of the result of a perfusion examination is decreased. Although the head of, for example, a patient is a motionless region, top priority is given to uniformity in the CT slice acquisition absolute time of a region undergoing a perfusion analysis in a head perfusion examination using the conventional computed tomography. As a result, the photographing range in the direction of a body axis becomes considerably narrow. As a result, it is impossible to diagnose the whole of diseased parts. In the worst case, it is known later that an important part has not been examined.

Concerning the conventional ECG-gated segment reconstruction and a technique relating to this, various algorithm or hardware attempts have been carried out to optimize the X-ray tube view angle of data acquired to form an ECG-gated segment reconstruction and heartbeat. Additionally, an attempt has been carried out to reduce a motion artifact and improve image quality.

On the other hand, the present invention aims to improve image quality in contrast while satisfactorily using a motion artifact even if temporal resolution is sacrificed.

For example, although a CT value of a diseased part is monitored and analyzed at time intervals in the perfusion examination, the fact that a motion artifact appears or disappears in response to the movement of an internal organ affects the CT value of the diseased part. This becomes a problem in perfusion analysis. In contrast with this, if a motion artifact constantly appears regardless of the movement of an internal organ as in the present invention, the CT value of the diseased part is not affected by its movement, and a wash-in & wash-out change in the contrast agent can be purely monitored.

DISCLOSURE OF THE INVENTION

The present invention has been made by paying attention to these respects. An object of the present invention is to stop the movement of the internal organs such as the heart and chest which report periodic movement and to obtain a dynamic image in which a contrast agent, a catheter, a tube, food and drink, etc., move through internal organs, such as the heart and the chest.

In the latest 64-row computed tomography in which 64 rows of scintillators are arranged in the direction of the axis of a CT gantry 20, an up to 40 mm-range in the axial direction (i.e., in the direction of the body axis of a patient) can be photographed by one rotation, and three-dimensional (solid) data can be obtained through so-called cine-scanning in which the gantry is rotated many times at the position in the same axial direction while fixing the table of the patient. Step & shoot scanning that repeatedly performs a step of subjecting a patient lying on a table to one-rotation computed tomography and then sliding the table for next computed tomography or helical scanning that performs CT scanning while moving the table has been carried out to obtain an image covering a wide range according to the conventional 16-row computed tomography or the computed tomography having a smaller number of rows than 16. However, images obtained by these scanning operations are different in time, and hence, if a moving object is photographed, a phase lag will degrade image quality, and it cannot be said that the image is a four-dimensional image obtained by adding the dimension of time to a three-dimensional image, although no problem will occur if the object is motionless.

On the other hand, in the 256-row computed tomography (256-row CT) now being developed, an image of a range of approximately 100 mm in the axial direction can be obtained by one rotation, and a four-dimensional image covering a wide range can be obtained. Therefore, as shown in FIG. 4 as an example of the head, in a conventional four-dimensional image, a diagnosis using an axial cross-section obtained by photographing a patient 10 in a slicing manner has been predominantly made as in FIG. 4(A). However, the 256-row CT is expected to make it possible to obtain four-dimensional images observed from various angles, such as a coronal cross-section observed from the front of the patient as in FIG. 4(B), a sagital cross-section observed from the direction of an arrow as in FIG. 4(C), or an oblique cross-section as in (D).

This 256-row CT technique can exhibit its ability especially in an examination using a contrast agent. For example, in a cardiac examination, efforts have been focused only on the direction of diagnosis in which temporal resolution is heightened by increasing the speed of half scanning or by shortening the CT rotation time and in which a cardiac movement is observed with the lapse of time. However, if an upside-down conception is formed and if the CT gantry is rotated with the same cycle as the heartbeat, the heart will be seen as if being stopped. As a matter of course, the temporal resolution is not high to its maximum, and hence a motion artifact appears.

The present invention has been made based on these findings. The object mentioned above is achieved by obtaining a dynamic image showing a transient phenomenon in which, when a repeatedly periodically moving site of a to-be-examined subject in a gantry is subjected to computed tomography and is reconstructed, the gantry is rotated in synchronization with the movement of the periodically moving site, and the periodic movement of the moving site has been stopped.

Additionally, in the present invention to achieve the object, a computed tomography apparatus for a moving site that subjects the repeatedly periodically moving site of a to-be-examined subject in a gantry to computed tomography so as to form a reconstruction of a segment includes a means for detecting the periodic movement of the moving site, a means for controlling the rotational speed of the gantry in synchronization with the periodic movement of the moving site, and a means for reconstructing resulting images and obtaining a dynamic image showing a transient phenomenon in which the periodic movement of the moving site has been stopped.

According to the present invention, a contrast examination is performed while taking advantage of the fact that an actually periodically moving site, such as the heart or the lungs, is seen as if being stopped even in a four-dimensional display, and diagnosis information that cannot be obtained through the conventional technique can be obtained by observing the wash-in, the wash-out, and the how-to-dye of a contrast agent concerning a transient phenomenon in which only the contrast agent flows through an internal organ whose movement has been stopped, and a muscular wall is perfused with the contrast agent. Therefore, a part of cancer or a part of a previous illness, such as cardiac infarction, can be seen by a difference in how to dye or how to flow, which is caused by cancer cells or the previous illness, and the state of the cardiac muscle is understood by the easiness of dyeing, and, as a result, a metabolic analysis can be made. Additionally, the movement of a catheter, the movement of a tube, the movement of food and drink, and the condition of digestion can be understood while curbing the influence of the periodically moving heart or the influence of a respiratory movement.

BEST MODE FOR CARRYING OUT THE INVENTION

An embodiment of the present invention will be hereinafter described in detail with reference to the drawings.

Figure 5:
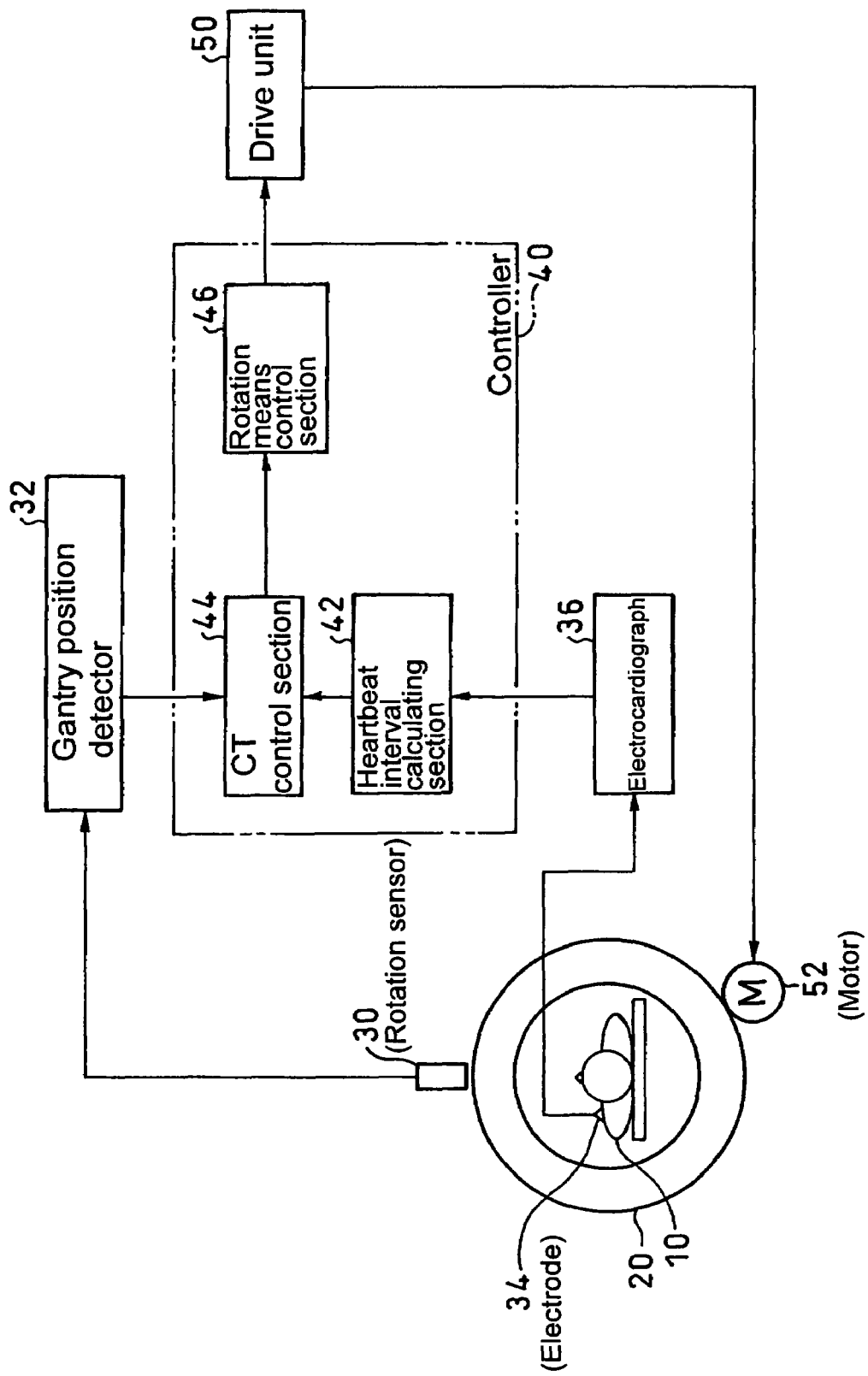
FIG. 5 is a block diagram showing a structure of an embodiment of a computed tomography apparatus according to the present invention.

As shown in FIG. 5, this embodiment is made up of a gantry position detecting means made up of, for example, a rotation sensor 30 and a gantry position detector 32 for detecting the rotational position of a CT gantry 20, a heartbeat measuring means made up of, for example, an electrode 34 attached to a body surface and an electrocardiograph 36 for measuring the heartbeat of a patient 10, and a controller 40 including a heartbeat interval calculating section 42 that calculates heartbeat intervals according to an output emitted from the heartbeat measuring means, a CT control section 44 that controls computed tomography according to an output emitted from the heartbeat interval calculating section 42 and an output emitted from the gantry position detecting means, and a rotation means control section 46 that controls a rotation means made up of, for example, a drive unit 50 and a motor 52 showing a direct drive motor for rotating the CT gantry 20 by an output emitted from the CT control section 44.

Figure 6:
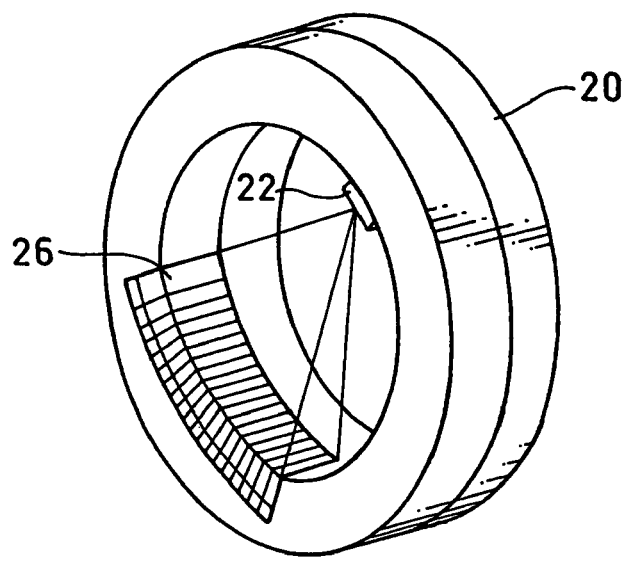
FIG. 6 is a perspective view showing an example of a CT gantry part.
Figure 7:
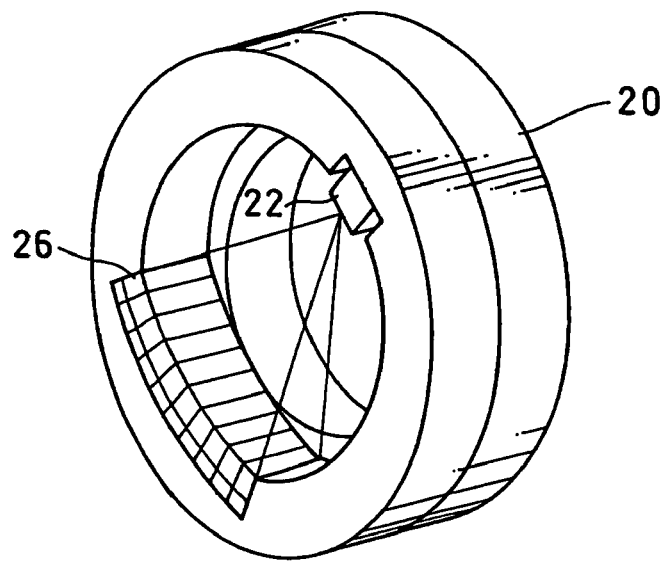
FIG. 7 is a perspective view showing another example of the CT gantry part.

As shown in FIG. 6 or FIG. 7, the CT gantry 20 has many blades 26 (e.g., 912 channels) arranged in the circumferential direction, each blade 26 including many scintillators (e.g., 256 scintillators) arranged in the axial direction, thus making it possible to perform two-dimensional measurement.

The blade 26 has a structure formed by removing the structure in the axial direction from a grid-like collimator. Aluminum, lead, molybdenum, or the like is used as a material for the blade 26. The width of the blade 26 is equal to the width of an element of the detector. The blade 26 includes scintillators each of which is made of, for example, ceramic, gadolinium, or xenon.

Hereinafter, the operation will be described.

Figure 1:
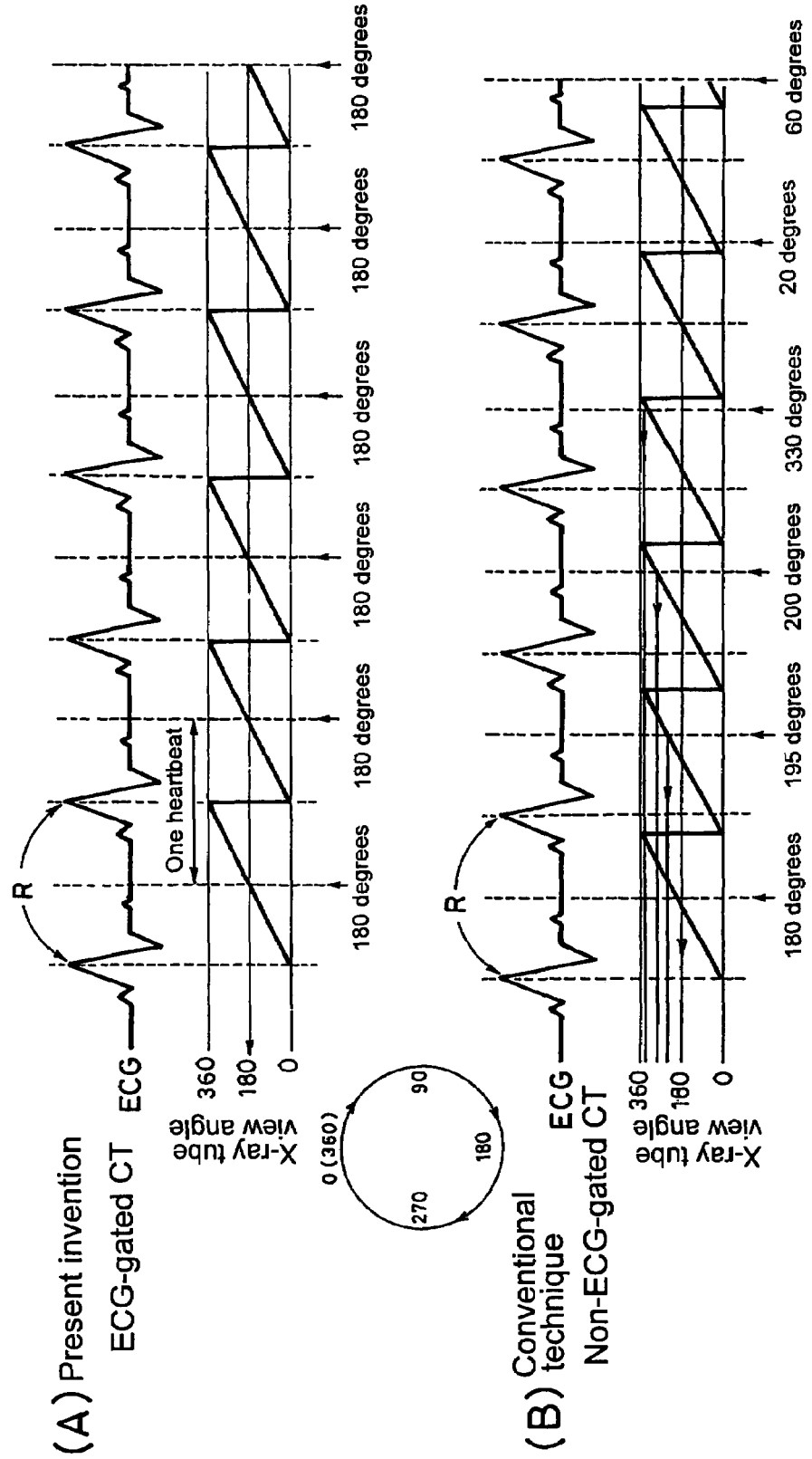
FIG. 1 is a time chart for explaining the principle of the present invention.
Figure 2:
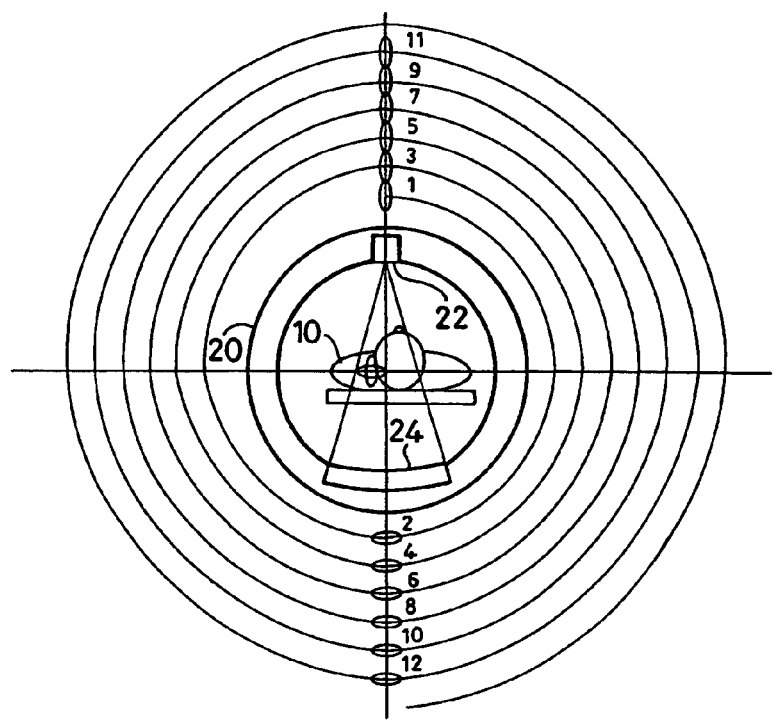
FIG. 2 is a front view of a CT gantry showing a situation of ECG-gated computed tomography.
Figure 3:
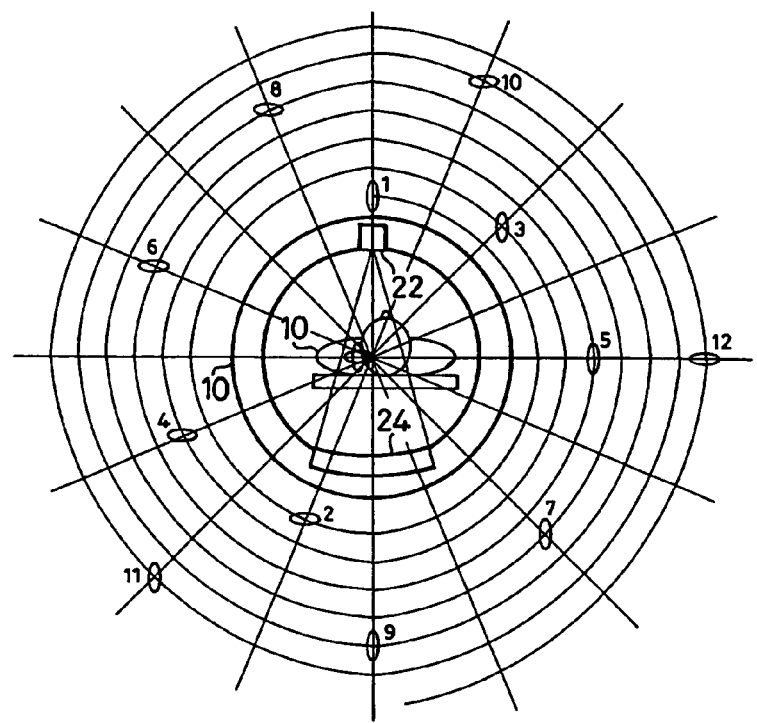
FIG. 3 is a front view of the CT gantry showing a situation of non-ECG-gated computed tomography.
Figure 4:
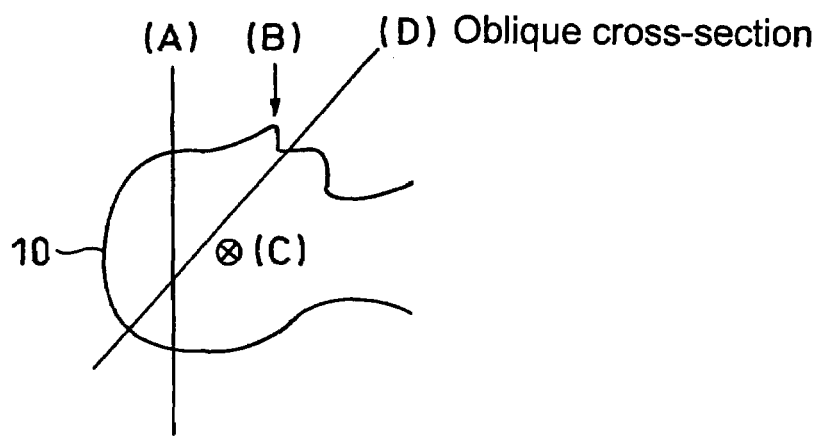
FIG. 4 shows examples of images obtained by computed tomography.
Figure 4:
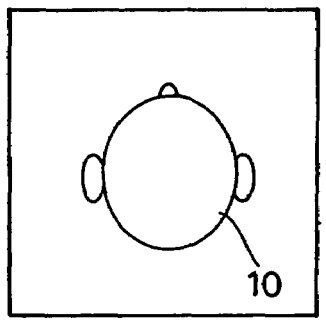
Figure 4:
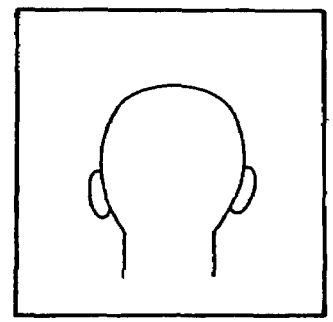
Figure 4:
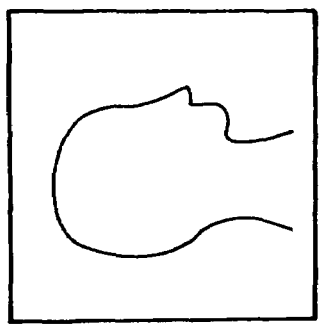

A schematic diagram of ECG-gated CT (i.e., ECG-gated Computed Tomography) according to the present invention and conventional non-ECG-gated CT is described in FIG. 1. In the ECG-gated CT of the present invention shown in FIG. 1(A), the CT apparatus makes one rotation for one heartbeat, and hence the CT apparatus is rotated from 0 degrees to 360 degrees between an R wave of an electrocardiogram (ECG) of the schematic diagram (i.e., the most pointed part in the ECG) and the next R wave. On the other hand, in the conventional non-ECG-gated CT shown in FIG. 1(B), the CT apparatus is rotated regardless of the heartbeat. In the non-ECG-gated CT, the CT apparatus does not necessarily make one rotation between the R waves, and is rotated at higher speed than the heartbeat in the example of FIG. 1(B).

In the conventional ECG-gated computed tomography, the heart having phases of parts pointed by arrows is subjected to computed tomography such that the rotation time of the CT apparatus does not coincide with the heartbeat as shown in FIG. 1(B), and, as a result, it is possible to obtain images all of which have mutually nonuniform tube view angles, such as 180 degrees, 195 degrees, 200 degrees, etc., in the tube view angle of computed tomography. Therefore, if images based on these nonuniform view angles are respectively collected by the quantity corresponding to one rotation (360 degrees), the images can be respectively reconstructed. However, according to the method of FIG. 1(B), an image of one phase of the heart is formed from nonuniform phases in absolute time, and hence a transient movement, such as the flow of a contrast agent, cannot be captured. In addition, the perfusion of the cardiac muscle cannot be seen. Moreover, in the conventional ECG-gated computed tomography, a contrast agent is injected so that the heart is always filled with the contrast agent during the computed tomography.

On the other hand, in the ECG-gated CT shown in FIG. 1(A), the parts pointed by the arrows are the same in the X-ray tube view angle (i.e., 180 degrees in the figure). In CT reconstruction, all pieces of information about projection images used for the reconstruction are reflected to form a reconstructed image. Therefore, in the ECG-gated CT, only information about one heartbeat is satisfactorily included in the one rotation of the CT apparatus. Therefore, even if the CT apparatus makes one rotation from the position of the part pointed by the arrow or even if the CT apparatus makes one rotation from the position slightly deviated from the arrow, information about one heartbeat will be infallibly included in such one rotation. In other words, even if the CT apparatus is rotated from any tube view angle, information about one heartbeat is included, and a motion artifact will appear in the same manner by the heartbeat.

When an animated or dynamic image is formed by continuously reconstructing these by the quantity corresponding to one rotation of the CT apparatus from a slightly deviated position of the X-ray tube view angle, a motion artifact caused by the heartbeat appears in the same manner, and hence the heart is seen as if being stopped. On the other hand, the movement of a contrast agent is transitory, and pieces of information about the contrast agent included during one rotation of the CT apparatus are nonuniform, and hence the movement of the contrast agent can be observed in the form of an animated image.

Additionally, if the heartbeat interval calculating section 42 is made up of an interval storing section and a forecasting section so as to always store heartbeat intervals going back to a consecutive predetermined number in the past in the interval storing section, and if a change appears while allowing the forecasting section to refer to the data stored therein, a mechanism can be formed such that the forecasting section analyzes its tendency and forecasts the next heartbeat intervals, and the forecast result is output to the CT control section 44, and, as a result, the rotational speed of the motor 52 is controlled so that the rotational speed of the gantry 20 follow this.

If the heartbeat has been disturbed to such a degree as to make it impossible to follow this because of, for example, arrhythmia, a corresponding image can be discarded.

Since the CT gantry 20 is directly driven by the motor 52 in this embodiment, high responsibility and high speed rotation can be achieved. A belt drive method can also be employed.

The heart has been taken as an example in the embodiment mentioned above. However, without being limited to the heart, the present invention can be applied to a general object that makes a periodic motion including a respiratory movement such as the lungs.

Data was acquired by use of a cardiac phantom. Herein, the phantom was moved at a heart rate of 45 times and 60 times per minute, and was photographed while injecting a contrast agent. What was moved was an inner, triangular pyramid part, which is moved rightwardly and leftwardly. The rotation time of the CT apparatus is one second per rotation, and has a synchronizing relationship with a case having a heart rate of 60 times.

Figure 8:
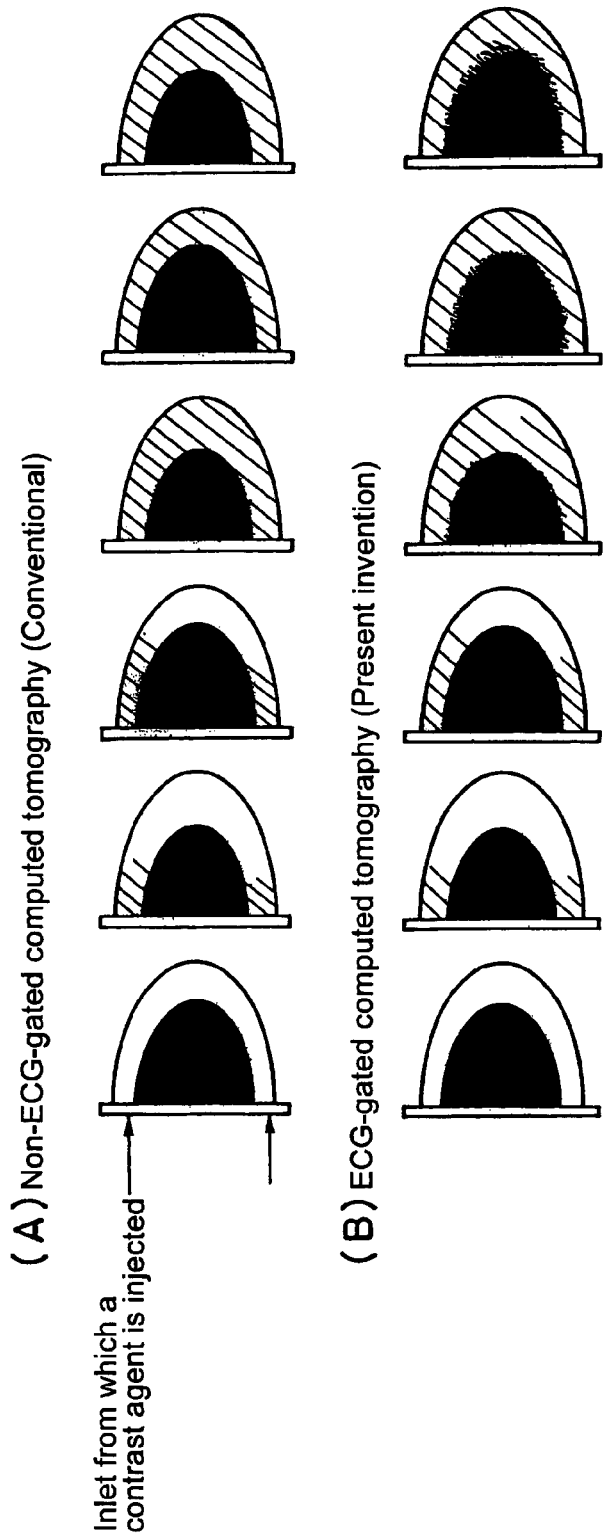
FIG. 8 is a sectional view showing a comparison between the embodiment of the present invention and an example of a conventional technique.

FIG. 8 is a coronal cross-section showing this situation. The upper part (A) of FIG. 8 shows images of conventional non-ECG-gated computed tomography, and the lower part (B) of FIG. 8 shows images of ECG-gated computed tomography according to the present invention. As the images move rightward, time advances. In the ECG-gated computed tomography according to the present invention, the moving part is merely doubly imaged even when this is filled with the contrast agent. On the other hand, in the conventional non-ECG-gated computed tomography, it is understood that this part is moving (first and second images from the right).

INDUSTRIAL APPLICABILITY

The present invention can be used for computed tomography for a moving site to form a segment reconstruction by subjecting a repeatedly periodically moving site of a to-be-examined subject in a gantry to computed tomography.

The invention claimed is:

1. A computed tomography method for obtaining an image of a periodically moving site of a to-be-examined subject in a gantry of a computed tomography machine so as to form a reconstructed dynamic image, comprising steps of:

rotating the gantry with a frequency substantially equal to a frequency of the periodically moving site, and obtaining the dynamic image that shows a transient phenomenon, wherein the dynamic image is obtained for points in time when the periodic movement of the moving site is at rest.

2. The computed tomography method for a moving site according to claim 1, wherein the computed tomography is performed with a 256-row CT.

3. The computed tomography method for a moving site according to claim 1, wherein, when the periodic movement is disturbed, a corresponding image is discarded.

4. The computed tomography method for a moving site according to claim 1, wherein the periodically moving site is a heart or lungs.

5. A computed tomography apparatus for obtaining an image of a periodically moving site of a to-be-examined subject in a gantry of the computed tomography apparatus so as to form a reconstructed dynamic image, the computed tomography apparatus comprising:

means for detecting a periodic movement of the moving site;

means for controlling the rotational speed of the gantry to have a frequency substantially equal to a frequency of the periodic movement of the moving site; and means for reconstructing resulting images and obtaining the dynamic image showing a transient phenomenon, wherein the resulting images are captured for points in time when the periodic movement of the moving site is at rest.

6. The computed tomography apparatus for a moving site according to claim 5, wherein the means for detecting the periodic movement of the moving site includes a heartbeat measuring means and a heartbeat interval calculating section that calculates heartbeat intervals in accordance with an output emitted from the heartbeat measuring means.

7. The computed tomography apparatus for a moving site according to claim 6, wherein the heartbeat interval calculating section is made up of an interval storing section and a forecasting section so as to always store heartbeat intervals going back to a consecutive predetermined number in the past in the interval storing section, and, when a change appears while allowing the forecasting section to refer to data stored therein, the forecasting section analyzes its tendency and forecasts a change in the next heartbeat interval.

8. The computed tomography apparatus for a moving site according to claim 5, wherein the means for controlling the rotational speed of the gantry includes:

a CT control section that controls the gantry in accordance with an output emitted from the means for detecting the periodic movement of the moving site and an output emitted from a gantry position detecting means for detecting a rotational position of the gantry; and a rotation means control section that rotates the gantry in accordance with an output emitted from the CT control section.

9. The computed tomography apparatus for a moving site according to claim 5, wherein the gantry is directly driven by a motor.

* * * * *